(12) United States Patent
Carr et al.

(10) Patent No.: US 8,142,389 B2
(45) Date of Patent: Mar. 27, 2012

(54) MICRODIALYSIS PROBE AND METHOD FOR THE PRODUCTION THEREOF

(75) Inventors: Matthew Carr, Cambridge (GB);
Bruno Reihl, Wilen bei Wollerau (CH);
Hanspeter Heiniger, Lotzwil (CH);
Stefan Jost, Mühleberg (CH)

(73) Assignee: Roche Diagnostics International AG, Steinhausen (CH)

( * ) Notice: Subject to any disclaimer, the term of this patent is extended or adjusted under 35 U.S.C. 154(b) by 1692 days.

(21) Appl. No.: 11/097,100

(22) Filed: Apr. 1, 2005

(65) Prior Publication Data

US 2005/0251087 A1    Nov. 10, 2005

Related U.S. Application Data

(63) Continuation of application No. PCT/EP03/11182, filed on Oct. 9, 2003.

(30) Foreign Application Priority Data

Oct. 9, 2002   (DE) ................................. 102 47 023

(51) Int. Cl.
*A61M 1/00* (2006.01)

(52) U.S. Cl. ............................................ 604/27; 604/29

(58) Field of Classification Search ................ 604/19, 604/24, 44, 27, 29, 507; 600/366; 210/321.6
See application file for complete search history.

(56) References Cited

U.S. PATENT DOCUMENTS

| | | | | |
|---|---|---|---|---|
| 3,512,517 A * | 5/1970 | Hall et al. | ...................... | 600/347 |
| 3,572,315 A * | 3/1971 | Cullen, II | ...................... | 600/364 |
| 3,893,448 A * | 7/1975 | Brantigan | ...................... | 600/364 |
| 3,981,297 A * | 9/1976 | Dunn et al. | ...................... | 600/364 |
| 4,016,863 A * | 4/1977 | Brantigan | ...................... | 600/366 |
| 4,516,580 A * | 5/1985 | Polanyi | ...................... | 600/364 |
| 4,901,727 A * | 2/1990 | Goodwin | ...................... | 600/364 |
| 5,372,582 A * | 12/1994 | Skrabal et al. | ...................... | 604/44 |
| 5,441,481 A * | 8/1995 | Mishra et al. | ...................... | 604/29 |
| 5,607,390 A * | 3/1997 | Patsalos et al. | ...................... | 604/29 |
| 5,735,832 A * | 4/1998 | Karlsson | ...................... | 604/524 |
| 5,741,284 A * | 4/1998 | Karlsson | ...................... | 604/160 |
| 6,199,262 B1 | 3/2001 | Martin | | |
| 6,346,090 B1 * | 2/2002 | Liska et al. | ...................... | 604/29 |
| 6,478,767 B1 | 11/2002 | O'Connell | | |

FOREIGN PATENT DOCUMENTS

| WO | WO 00/10464 | 3/2000 |
|---|---|---|
| WO | WO 01/10483 | 2/2001 |
| WO | 2004/033000 | 4/2004 |

* cited by examiner

*Primary Examiner* — Jackie Ho
*Assistant Examiner* — Michael J Anderson
(74) *Attorney, Agent, or Firm* — Dinsmore & Shohl LLP (57) ABSTRACT

A microdialysis probe including a probe body, a supply line and a discharge line for a perfusion solution and a dialysis membrane, wherein a probe needle for introduction into a tissue is provided by a generally elongate frame. The frame has at least one recess at least partially open for receiving at least a portion of the supply and discharge lines. The invention encompasses a method for making such a probe, wherein the method includes arranging a dialysis membrane on a shaping device, shaping the dialysis membrane in a selected shape, applying an adhesive agent to the dialysis membrane to keep the membrane in the selected shape, and separating the dialysis membrane and the shaping devices after the adhesive agent has been applied.

31 Claims, 4 Drawing Sheets

MICRODIALYSIS PROBE AND METHOD FOR THE PRODUCTION THEREOF

CROSS-REFERENCE TO RELATED APPLICATION(S)

This application is a continuation of International Patent Application No. PCT/EP2003/011182, filed on Oct. 9, 2003, which claims priority to German Application No. 102 47 023.5, filed Oct. 9, 2002, the contents of which are incorporated in their entirety by reference herein.

BACKGROUND

The invention relates to microdialysis probes, embodiments of such probes and to methods for the production or making of such probes.

In medical technology, microdialysis probes are used, for example, to measure concentrations of defined substances dissolved in tissue fluids. A conventional microdialysis probe is typically provided by a probe body and a probe needle protruding from the latter. Upon insertion into a tissue, for example human or animal body tissue, the probe needle is received completely by the tissue and the probe body remains on the surface of the tissue. The probe needle is typically provided with supply and discharge lines, extending concentrically for example, for a perfusion solution, and an area at the end of the supply line has a dialysis membrane. In dialysis, a concentration equalization takes place at the dialysis membrane between the perfusion solution and the tissue environment into which the probe needle has been introduced, and permeable dissolved substances are exchanged. After the concentration equalization, the perfusion solution is returned via the discharge line.

A construction of a microdialysis probe is known from DE 199 37 099 A1, in which the supply line and the discharge line are provided next to one another in the form of separate hollow channels. For this purpose, two tubes are arranged next to one another. The tubes, by the way they are cut, form a common tip for introduction into a tissue and, in an area at which they adjoin, each has an opening to allow the perfusion solution to pass from one tube into the other. A dialysis hollow fiber is arranged inside one tube, and, in the area of the hollow fiber, the tube has recesses in sections for bringing the hollow fiber into contact with the tissue environment. In another embodiment, a star-shaped support structure is introduced into a dialysis hollow fiber. The inner surface of the hollow fiber lies on the tips of the support structure, so that channel passages form between the support structure and the hollow fiber. In an area at the tip of the probe needle, the support structure is interrupted in such a way that the hollow channels are interconnected. One of the hollow channels serves as a supply line for the perfusion solution which, at the transition area of the channels, is passed into the other channels which serve as discharge line.

In the above and other microdialysis probes according to the prior art, an extensive support structure such as a system of tubes is provided, as a result of which a dialysis membrane is not unnecessarily loaded by pressure from the tissue or during penetration into the tissue. The outer surface of the support structure, however, is then, by comparison, much greater than an area left free for dialysis. To achieve a sufficient dialysis surface, the probe needles therefore have to be made correspondingly long and thick. In the case of a support structure in the inside of a dialysis hollow fiber, a dialysis surface is of course considerably increased, but the dialysis membrane does not have sufficient protection against external influences.

In the production of such microdialysis probes, a large number of individual parts have to be fitted into or onto one another, with the result that a large number of transition areas or abutting edges arise between the individual parts, in particular between a dialysis membrane and a support structure. Since the material of a dialysis membrane swells and expands when introduced into a tissue, that is to say when it becomes moist, transition areas between the material of the membrane and the support structure represent weak points of a microdialysis probe. In general, although the material of a dialysis membrane is flexible, it does not automatically remain in a bent or curved shape, and this means that sufficient supporting and securing measures have to be taken to keep a microdialysis membrane in a desired shape. These support structures, however, in most cases severely limit the free dialysis area.

SUMMARY

It is an object of the present invention to provide a microdialysis probe which overcomes the abovementioned disadvantages of the prior art. In particular, the size of the dialysis surface and the structural length should be optimized, the wearing comfort increased, and the number of individual parts reduced, while at the same time ensuring an optimal flow of a perfusion solution.

A further object of the present invention is to provide a method for the production of a microdialysis probe, by which method a dialysis membrane can be brought in a simple manner into a desired shape and/or profile, and fixed in the shape and/or profile with only a small number of individual parts being used.

According to the present invention, these and other objects are achieved by a microdialysis probe with a probe body and a probe needle which protrudes from the probe body and is introduced into a tissue, a supply line and a discharge line for a perfusion solution, and a dialysis membrane, the probe needle being provided by an elongate frame which, in one or more of its circumferential surfaces, has at least one recess which is open to an outside of the frame and which is provided for receiving at least a portion of the supply and discharge lines.

In one embodiment, the present invention comprises a microdialysis probe including a probe body, a supply line and a discharge line for a perfusion solution and a dialysis membrane, wherein a probe needle for introduction into a tissue is provided by a generally elongate frame. The frame has at least one recess at least partially open for receiving at least a portion of the supply and discharge lines. The invention encompasses a method for making such a probe, wherein the method includes arranging a dialysis membrane on a shaping device, shaping the dialysis membrane in a selected shape, applying an adhesive agent to the dialysis membrane to keep the membrane in the selected shape, and separating the dialysis membrane and the shaping devices after the adhesive agent has been applied.

In one embodiment, the present invention provides a microdialysis probe comprising a probe body, a supply line and a discharge line for a perfusion solution and a dialysis membrane, wherein a probe needle for introduction into a tissue is provided via a generally flat, elongated frame. The frame has at least one recess at least partially open for receiving at least a portion of the supply and discharge lines. The invention encompasses a method for making such a probe, wherein the method comprises the steps of arranging the dialysis membrane on a shaping means such that it is at least partially adjacent thereto, giving the dialysis membrane a specific shape by bending the shaping means, applying an adhesive agent at a bending point of the dialysis membrane to keep or retain the membrane in the specific shape, and removing the shaping means from the dialysis membrane after the adhesive agent has been applied.

The present invention encompasses methods for making a microdialysis probe, including a method for making the probe described in the immediately preceeding paragraph. In one embodiment, the method comprises the steps of providing a shaping means on which the dialysis membrane is at least partially brought to bear, bringing the dialysis membrane into a predetermined shape by bending the shaping means, maintaining the membrane in the predetermined shape by applying an adhesive agent at least partially at a bend point of the dialysis membrane, and removing the shaping means from the dialysis membrane after the adhesive agent has been applied.

A microdialysis probe according to the invention has a probe body from which a probe needle protrudes which can be introduced into a tissue. The microdialysis probe also has a supply line and a discharge line for a perfusion solution, and a dialysis membrane, and the membrane can form at least part of the supply and/or discharge lines. According to one embodiment of the invention, the probe needle is formed by an elongated frame. In one or more of its surfaces, the frame has at least one recess which is open to the surroundings, i.e., to an outside or exterior of the frame, and which is provided for receiving the supply line and/or the discharge line for a perfusion liquid.

In some embodiments, the frame preferably has a rectangular cross section with a smaller height in comparison to the width. The height and width should be chosen as small as possible since the frame is used for introduction into a human tissue and, in this way, the unpleasantness for the user is minimized. Of course, the frame can also have any other desired cross section. At a distal end portion remote from the probe body, a tip for introduction into the tissue is formed on the frame. The tip is preferably formed by a tapering of the narrow opposite faces of the frame in the direction of the center of the frame, such as is described for example in the patent application entitled "Needle tip" from the Applicant, which application is filed by the Applicant of the present application and bears the same application date. The frame is preferably made in one piece as a shaped part. The frame can form part of the probe body, for example by widening it at its end remote from the tip, in such a way that the widened area forms a housing side of the probe body. The frame preferably has at least partial flexibility, as a result of which it can in principle be bent to a certain extent, but does not remain in a bent position. This flexibility means that the probe needle can yield to small movements or pressures of the tissue, as a result of which the microdialysis probe is more easily tolerated by the user. The frame is preferably made of plastic that permits this flexibility. However, the frame can also be made of metal. Moreover, a metal tip can be fitted on a plastic frame to make insertion into a tissue easier.

On at least one circumferential surface of the frame, i.e., for example on one of the side faces extending in the longitudinal direction of a rectangular frame, preferably on the wider side face, open recesses are provided for receiving the supply line and preferably also the discharge line, these open recesses extending substantially in the longitudinal direction of the elongate frame. Accordingly, a recess or relieved area is integrated into or formed by the frame, that is to say, it is let into the frame. The supply line and the discharge line preferably merge into one another at a reverse turn which lies inside a recess. The recesses are introduced into the frame by an etching technique, for example, although other techniques such as milling or cutting can also be used. In a frame which also forms part of the probe body, a recess preferably starts already in the part forming the probe body. A recess also advantageously extends as far as the tip of the frame, that is to say to the distal end portion of the probe needle. In this way, by means of the recess in the frame, an opening can be formed between the frame and the probe body and lies inside the cross-sectional surface of the frame.

In one embodiment of the present invention, the reverse turn between the supply line and the discharge line is formed by the course of the recess. For this purpose, at least one recess can be formed in the frame in such a way that a first depression extending along the frame forms the supply line, and a second depression arranged next to the first depression forms the discharge line. The first depression and second depression merge into one another in a distal end portion of the frame and thereby form the reverse turn. The first depression, the second depression and the reverse turn together form the recess according to the invention. The cross section of the depressions in the frame is preferably rounded at its corners lying in the inside of the frame. When a liquid flows through these depressions, the rounded corners afford a favorable flow behavior of the liquid. The cross section of the depressions can, however, have any other shape, as long as it is open upward from the circumference surface of the frame. The reverse turn preferably runs in an arc of a circle of 180° from the first depression to the second depression. A round profile of the reverse turn ensures a favorable flow behavior of a liquid running through the recess. The first and second depressions are preferably arranged on the same circumference surface of the frame. However, if the frame has several circumference surfaces extending in the longitudinal direction of the frame, for example a rectangular frame, the depressions can also be provided on different sides, in particular on opposite sides. In this case, the reverse turn between the supply line and the discharge line can be provided by a bore which runs through the frame and connects the first and second depressions.

In one embodiment, at least one dialysis membrane in the form of a membrane sheet or membrane layer is applied over a recess on a surface of the frame. The membrane layer is connected to the frame across the entire surface edge and all round the recess, for example by lamination or gluing. In this way, a hollow channel for the supply line and discharge line is formed under the dialysis membrane in the area or space between the recess and the membrane.

It is preferable to use a single membrane layer which already starts in a frame area inside the probe body, extends across the entire recess and ends at the distal end portion of the frame. However, if recesses or depressions are formed on different sides of the frame, it is advantageous to use a separate membrane layer for each side.

According to another embodiment of the present invention, the frame has at least one recess which at least partially cuts through the frame so that a longitudinally extending slit is formed inside the frame. The slit is preferably introduced by etching into a frame made of plastic, for example. It is advantageous here if the side walls of the slit which lie to the inside of the slit have a concave shape. The walls, however, can have any other desired shape. The slit preferably starts in a frame area inside the probe body, as a result of which an opening can be formed on the probe body within the cross section of the frame. The slit preferably ends with a rounded area shortly before the distal end portion of the frame.

A dialysis membrane in the form of a hollow fiber is arranged in the slit in such a way that it is turned back at a reverse turn area and, in this way, two stretches or lengths of hollow fiber come to lie or are positioned approximately next to one another. The reverse turn area is preferably provided in the rounding of the slit at the distal end portion of the frame. In this reverse turn area, the hollow fiber membrane is bent through 180° so that two stretches or lengths of hollow fiber are next to one another, one forming the supply line and the other forming the discharge line for a perfusion solution. The dialysis membrane hollow fiber is secured in the reverse turn area, for example by an adhesive agent or, alternatively, by a pin around which it is placed and which is connected to the frame.

The height of the cross section of the frame preferably has substantially the same dimension as the external diameter of the hollow fiber membrane. The width of the slit is advantageously substantially exactly twice the external diameter of the hollow fiber membrane. In this way, the two hollow fiber membranes extending next to one another substantially exactly fill the space formed in the frame by the slit, without the hollow fiber membrane being deformed or protruding past the frame surface. If the slit already starts in a frame area inside the probe body, it is possible for a one-piece hollow fiber membrane to emerge from the probe body and extend along the slit as far as the reverse turn area and then back again into the probe body. In this way, no connection points at all are needed inside the probe needle, and instead the dialysis membrane surface is formed by a single continuous surface within the tissue. The hollow fiber membrane preferably lies free between the reverse turn area and its starting area or end area, that is to say that, apart from the securing in the reverse turn area, no further points of securing for the hollow fiber membrane are needed in the probe needle. In one preferred embodiment, the hollow fiber membrane emerges from the probe body through an opening, which has been made possible by the frame and the probe body via a slit, out of the probe body and, after the reverse turn area, it passes back through such an opening into the probe body. In a plane of the surface of the frame, several flat projections can extend over the slit and the secured hollow fiber membrane and serve to guide and secure the hollow fiber lying free in this part.

It is possible to provide a separating surface between the stretch of hollow fiber for the supply line and the stretch of hollow fiber for the discharge line. By means of such a separating surface, a continuous concentration equalization of a perfusion solution on the inward path in the supply line and on the outward path in the discharge line could be guaranteed without an interaction taking place between the supply line and the discharge line on account of the concentration difference in these lines.

In order to avoid this kind of cross diffusion between the supply line and the discharge line, it is also possible for the hollow fiber dialysis membrane to be surrounded by a nonpermeable layer along a partial stretch or length of the supply or discharge line, so that no diffusion takes place in this area. For this purpose, the membrane, before being introduced into the frame, is closed along a partial stretch with plastic for example, preferably a biocompatible adhesive. The closed partial stretch advantageously amounts to ca. 20 to 50% of the total length of the hollow fiber for a supply line or discharge line. To suppress cross diffusion as efficiently as possible, a closed partial stretch begins immediately after the emergence of the dialysis hollow fiber membrane from the probe body, so that the closed part is arranged on the probe body. The remaining part in the direction of the needle tip remains open for dialysis. Such an arrangement of the closed stretch of hollow fiber leaves the supply line and discharge line free in the distal end portion of the dialysis needle which is introduced farthest into the tissue and around which the greatest amount of liquid exchange takes place. Moreover, the closed partial stretch of hollow fiber is preferably provided on the supply line, and the discharge line along the entire stretch from the needle tip to the probe body is left untreated. A colored layer is preferably used so that positioning of the membrane inside the frame at a desired site is made easier.

In the illustrative embodiments mentioned, a dialysis surface, formed by the dialysis membrane, extends the entire length of the recess or relieved area, which preferably starts inside the probe body. The dialysis surface therefore extends the entire length of the probe needle. Therefore, the length of the probe needle does not have to be any longer than the stretch or length needed for sufficient dialysis. Moreover, especially in the embodiment with a slit and a hollow fiber membrane, the dialysis surface is maximized since there are virtually no support measures or securing devices to restrict the dialysis surface. For dialysis, this therefore gives an optimal ratio of membrane surface to conduit volume, i.e., the perfusion solution led through can come into contact with the tissue across a maximized surface area, and there are absolutely no lost spaces inside the lines. In the illustrative embodiments mentioned, the dialysis procedure is possible both in the supply line and also in the discharge line, that is to say twice along the entire needle length. For this reason, the overall needle length, that is to say the length of the frame, can be further reduced. In a microdialysis membrane according to the invention, the number of transitions between a dialysis membrane and other needle components is also reduced, and, especially in the case of a frame with a slit and a hollow fiber membrane, there are no longer any such transitions. For a user, the wearing comfort of a microdialysis probe according to the invention is enhanced because the probe can be made particularly slender and short, and the probe is also more easily tolerated because of the flexibility of the needle.

In principle, it would also be conceivable to configure a recess so that it is only partially open to the outside and to form another part, for example, as a central bore through the channel. It is also conceivable, for example, to provide one supply line and several discharge lines. For this purpose, three depressions, for example, could be provided in a frame, with one depression merging into the two other depressions via a reverse turn. In this case, for example, a frame with a triangular or hexagonal cross section could be used which has a depression on each side, with one depression being connected to the two other depressions via a respective bore. In an embodiment with a recess in the form of a depression, it is also possible in principle, instead of applying a membrane layer over the depression, to lay a hollow fiber membrane inside the depression.

The frame is preferably flexible to the extent that it still has sufficient stiffness to be used as a probe needle which itself pierces the skin. However, it is of course also possible to place the frame in the tissue using an insertion aid, and then to remove the insertion aid after insertion.

In addition to its use for measuring concentrations, a microdialysis probe according to the invention is also suitable for measuring viscosity inside a tissue.

Objects of the present invention are also achieved by a method for the production of a microdialysis probe, in which method a dialysis membrane is brought into a predetermined and at least partially bent shape and is arranged in or on a frame forming a probe needle. For this purpose, the dialysis membrane initially bears on or contacts a shaping means and is then brought into a predetermined shape by bending or forming the shaping means. An adhesive agent or connecting means, for example an adhesive cement or glue, is then applied at least partially at a bend point of the dialysis membrane, so that the membrane is maintained in the predetermined shape. The shaping means is removed from the dialysis membrane after the adhesive agent has been applied.

In a preferred method, the dialysis membrane is present in the form of a hollow fiber through which a filament or a thread or a wire is passed as the shaping means. It is advantageous here for the filament to have an external diameter which corresponds approximately to the internal diameter of the membrane hollow fiber, but leaves enough space free to be able to remove the filament as soon as the membrane hollow fiber is secured in its final shape.

A prefabricated frame or prefabricated support structure is preferably used whose configuration determines the shaping of the dialysis membrane or of the membrane hollow fiber. The dialysis membrane can then be fitted into this prefabricated shape with the aid of the shaping means and can be maintained in this shape with the aid of the adhesive agent at its bend points, which adhesive agent can connect the dialysis membrane at least partly to the frame.

A nylon thread is preferably used as filament. The adhesive agent can include cyanoacrylate, silicone or epoxide, for example. It is also possible to use, as the adhesive agent, a one-sided or two-sided pressure-sensitive adhesive tape material. The adhesive agent should be adapted to the material of the frame and of the dialysis membrane so as to be able to produce a rapid and yet strong connection.

It is also possible in principle for the frame to be formed by the adhesive agent, i.e., by the material of the adhesive agent. In this case, the dialysis membrane can be brought into a predetermined shape by the shaping means, and the adhesive agent can then be applied at least partly to the dialysis membrane in such a way that the shape of the adhesive agent corresponds to a desired shape of a dialysis needle. For this purpose, it is advantageous if the adhesive agent has a stiffening action after application to the dialysis membrane. Care must be taken to ensure that a sufficient surface area of the dialysis membrane remains free for the dialysis. It is possible to apply the adhesive agent in a kind of tube shape around the dialysis membrane and then to create the desired shape, for example by etching or cutting.

It is also possible to use a membrane layer or membrane sheet which is brought into a desired shape by a plate serving as shaping means. In this way it is possible to bring large surface areas of a dialysis membrane into a desired bent shape, as may be necessary, for example, for winding it around frames or support structures. For the method according to the present invention, the adhesive agent may be applied first to the frame or to the dialysis membrane. When choosing the securing points, the fact that the membrane expands in the moist state must be taken into consideration to ensure that, after being secured, it does not cause any kinks or folds that could interfere with the desired shape of the membrane.

A microdialysis probe in an above-described embodiment can be produced, for example, by the method according to the invention. If, for example, a flat elongate frame with a recess in the form of a slit for the supply line and discharge line of a perfusion solution is used for a probe needle, the method according to the invention can be used to place a hollow fiber membrane inside the slit, with a shape corresponding to the shape defined by the slit. For this purpose, the hollow fiber membrane, with the aid of a filament running through it, is arranged in the slit of the frame in such a way that two stretches or lengths of hollow fiber lie next to one another and form a 180° loop at a rounded end of the slit before a distal end portion of the frame. The adhesive agent is then applied at least to the rounded part of the slit between the frame and the hollow fiber membrane. After the securing, curing or stiffening action of the adhesive agent has taken place, the filament can be removed from the membrane hollow fiber. In this way, the membrane hollow fiber is laid in the slit and secured therein. The two ends of the membrane hollow fiber preferably extend into a probe body. After insertion into a tissue, such a probe needle of a microdialysis probe has no connection points at all inside the tissue.

Before the hollow fiber membrane is inserted into the frame, it is advantageous for a partial stretch or length of the hollow fiber membrane to be surrounded with a non-permeable layer, for example a biocompatible glue. The glue closes the dialysis membrane along this partial stretch, so that no exchange takes place along said stretch. When fitting the hollow fiber membrane into the frame, this closed partial stretch is preferably arranged at the point of emergence of the supply line from the probe body. Between this supply line and a stretch or length of hollow fiber extending alongside it for the discharge line, no interaction can take place along the closed partial stretch in the area where the supply line and discharge line are adjacent, with the result that cross diffusion from the supply line to the discharge line is suppressed. A colored layer is preferably chosen so that, when fitting the hollow fiber dialysis membrane, it is easier to position the closed partial stretch at the desired location in the frame.

DETAILED DESCRIPTION OF THE DRAWINGS

Figure 1:
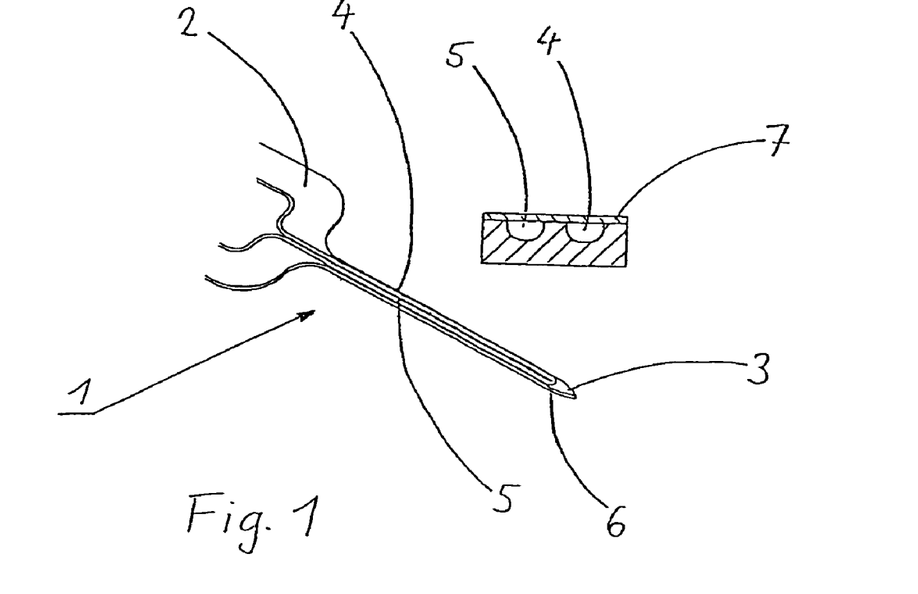
FIG. 1, including FIGS. 1a and b, provides a perspective view and a cross section of an embodiment of a microdialysis probe according to the present invention, FIG. 2, including FIGS. 2a and b, provides a perspective view and a cross section of another embodiment according to the present invention.

FIG. 1 shows a probe needle of a microdialysis probe according to the invention, provided by a flat elongate frame 1. In a rear portion, the frame 1 has a widened area 2 as part of a probe body. In a distal end portion, a tip 3 for introduction into a tissue is formed on the frame 1. The cross section of the frame 1 is rectangular and has, for example, a height of 0.3 mm and a width of 1.0 mm. The length of the frame 1 is adapted to the required dialysis surface and is, for example, ca. 10.0 mm. Formed in a circumference surface of the frame 1, and running along the frame 1, there are a first depression 4 and a second depression 5 which runs parallel alongside the first depression 4. As can be seen from the cross section in FIG. 1, the edges between a bottom and the side walls of the depressions are rounded. Before the distal end portion of the frame 1, near the tip 3, the first depression 4 and the second depression 5 merge into one another at a reverse turn 6. The reverse turn is designed as a semicircular depression which opens both into the first depression 4 and also into the second depression 5 so that these are interconnected. The first depression 4, the second depression 5 and the reverse turn 6 form a recess which is open toward an outside of the frame 1 and which, according to the present invention, receives a supply line and a discharge line for a perfusion solution of the microdialysis probe. The first depression 4 can form the supply line, and the second depression 5 can form the discharge line, or vice versa. As will be evident from the drawing, the rectilinear areas of the depressions 4 and 5 extend right into the widened area 2 of the frame, so that, when the microdialysis probe is assembled, that is to say when the probe body is connected to the probe needle, the depressions 4 and 5 run right into the probe body. A dialysis membrane layer 7 is applied on the circumference surface of the frame 1 in which the depressions 4 and 5 are arranged. As will be seen from the cross section in FIG. 1, the membrane layer 7 extends across the entire width of the frame 1 and covers the depressions 4 and 5. At the contact surfaces where the membrane layer 7 lies on the surface of the frame 1, the layer is connected to the frame, for example by lamination. Between the membrane layer and the frame 1, a hollow channel is formed through which the perfusion solution can be guided. After the dialysis probe has been introduced into a tissue, the whole needle area is surrounded by the tissue. On passing a perfusion solution through the hollow channel, a concentration exchange between the tissue environment and the perfusion solution can take place along the entire length of the frame 1 and across the entire width of the depressions 4 and 5.

The material used for the membrane layer can, for example, be regenerated cellulose, for instance from Medicell or Spektrum Labs. The frame 1 can be made, for example, of steel, a liquid-crystalline polymer or polybutylene terephthalate (PBT). However, comparable metals and plastics are also suitable for the production of the frame. Flexible materials are advantageously used in order to give the probe needle some pliability, which makes the needle more comfortable for the user.

Figure 2:
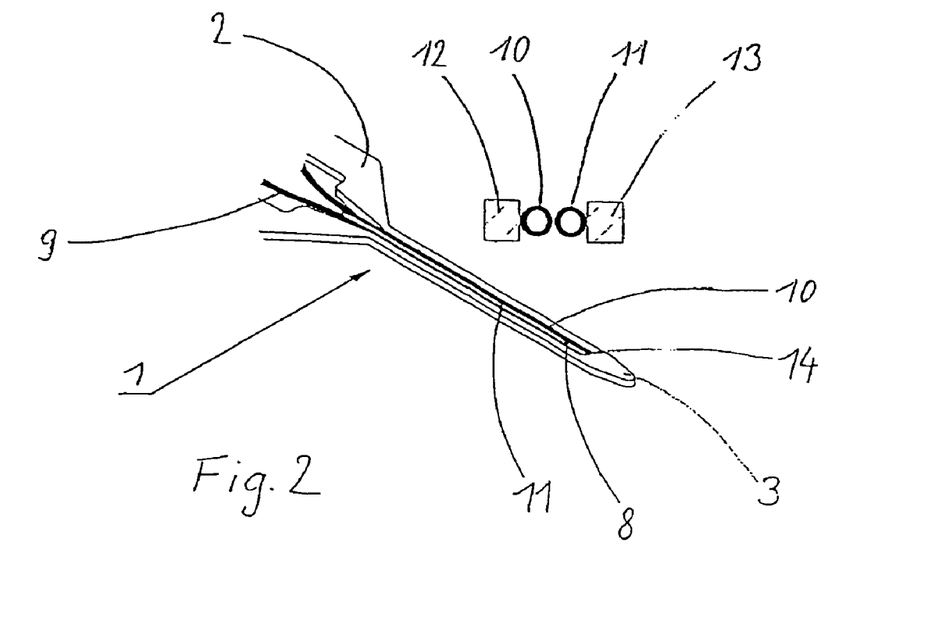

FIG. 2 shows a second illustrative embodiment for an elongate frame 1 of a microdialysis probe according to the invention. The frame 1 is divided in the longitudinal direction, from a widened area 2 as far as the frame tip 3, by a recess forming a slit 8 in said frame. The slit 8 also widens in the widened area 2. A dialysis membrane in the form of a hollow fiber 9 is arranged inside the slit 8 in such a way that two stretches of hollow fiber 10 and 11 come to lie next to one another. The stretches of hollow fiber 10 and 11 form the supply line and discharge line for the perfusion solution into the probe needle.

As will be seen from the cross section in FIG. 2, the frame 1 is partly divided into two branches 12 and 13 by the slit 8. The cross section of the stretches of hollow fiber 10 and 11 is shown between these branches 12 and 13. The space between the branches 12 and 13 corresponds to twice the size of the external diameter of the membrane hollow fiber, and the height of the branches 12 and 13 or of the frame 1 corresponds to the external diameter of the membrane hollow fiber 9. It should be noted that the membrane hollow fiber expands in the moist state and the diameter then widens. The frame 1 is adapted to the dimensions of an expanded or swollen membrane hollow fiber.

The membrane hollow fiber can be introduced into the slit 8 using a method according to the present invention for example. The membrane hollow fiber 9, at a reverse turn or loop 14 of the membrane, is secured on a rounded end area of the slit before the distal end portion of the frame. The stretches of hollow fiber 10 and 11 can then come to lie without further securing between the branches 12 and 13. On inserting the probe needle into a tissue, the frame 1 penetrates into said tissue as far as the widened area 2. In the process, the membrane hollow fiber 9 runs continuously into the tissue and out of it. There are therefore no transition points between the material of the membrane and the material of the frame. As is shown in FIG. 2, the hollow fiber 9, starting from the wider slit area in the widened area 2, is introduced into the slit 8 of the frame 1. Inside the tissue, the tissue environment on two sides of the frame 1 comes into contact with the dialysis membrane, as a result of which the surface area of the membrane layer taking part in the dialysis or concentration exchange is further increased in comparison to the embodiment according to FIG. 1. Moreover, the concentration equalization can take place both in the supply line and also in the discharge line of the perfusion liquid.

The needle tip 3 is formed both in FIG. 1 and in FIG. 2 by a tapering-in of the narrow faces of the frame 1, for example as is set out in the aforementioned patent application.

Figure 3:
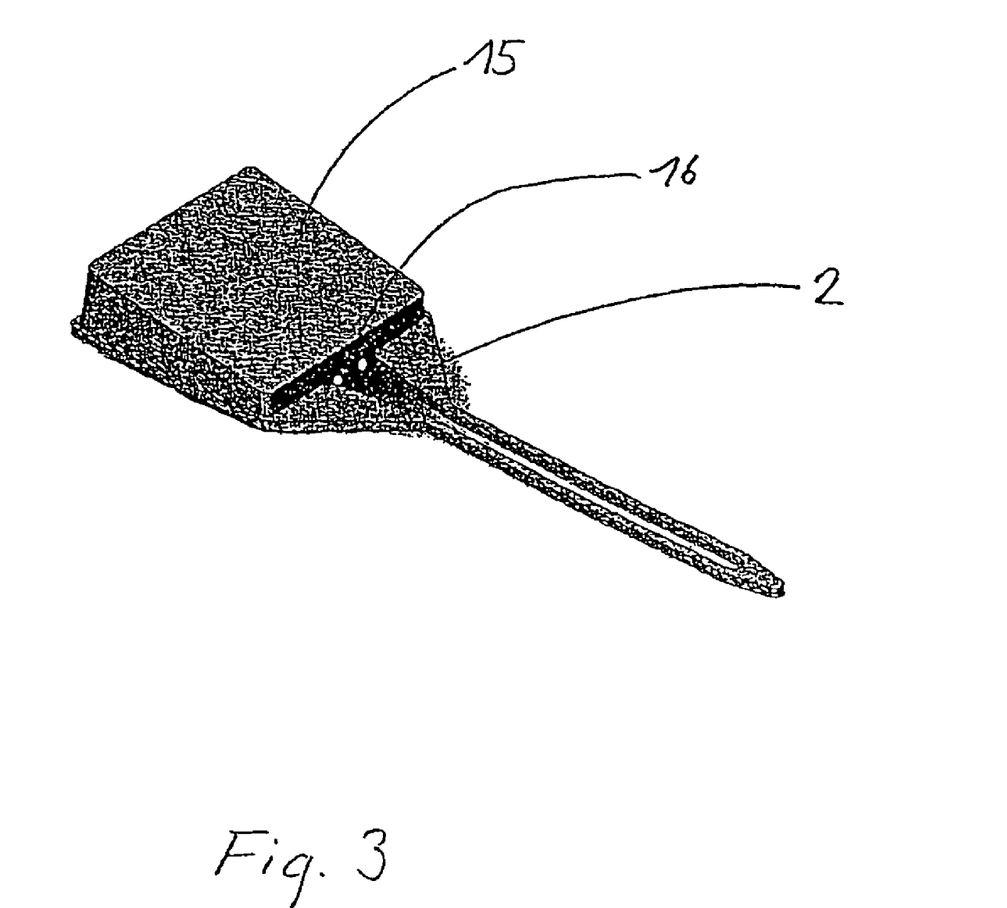
FIG. 3 is a perspective view of a microdialysis probe in the illustrative embodiment of FIG. 2 with an exemplary probe body, FIG. 4, including

FIG. 3 shows an embodiment of the frame 1 from FIG. 2, with a housing part 15 fitted on its widened area 2. The widened area 2 and the housing part 15 thus form the probe body. The housing part 15 is designed in such a way that it can be fitted with its underside onto the widened area 2 of the frame 1. A projection 16 extends into the widened area of the slit 8 and has two round openings through which the stretches of hollow fiber 10 and 11 can be guided. Moreover, at the transition between membrane and probe body, there are no connection points at all between the material of the membrane and the material of the probe body, and instead a perfusion solution comes into contact exclusively with the material of the membrane.

Figures 4A, 4B, 4C:
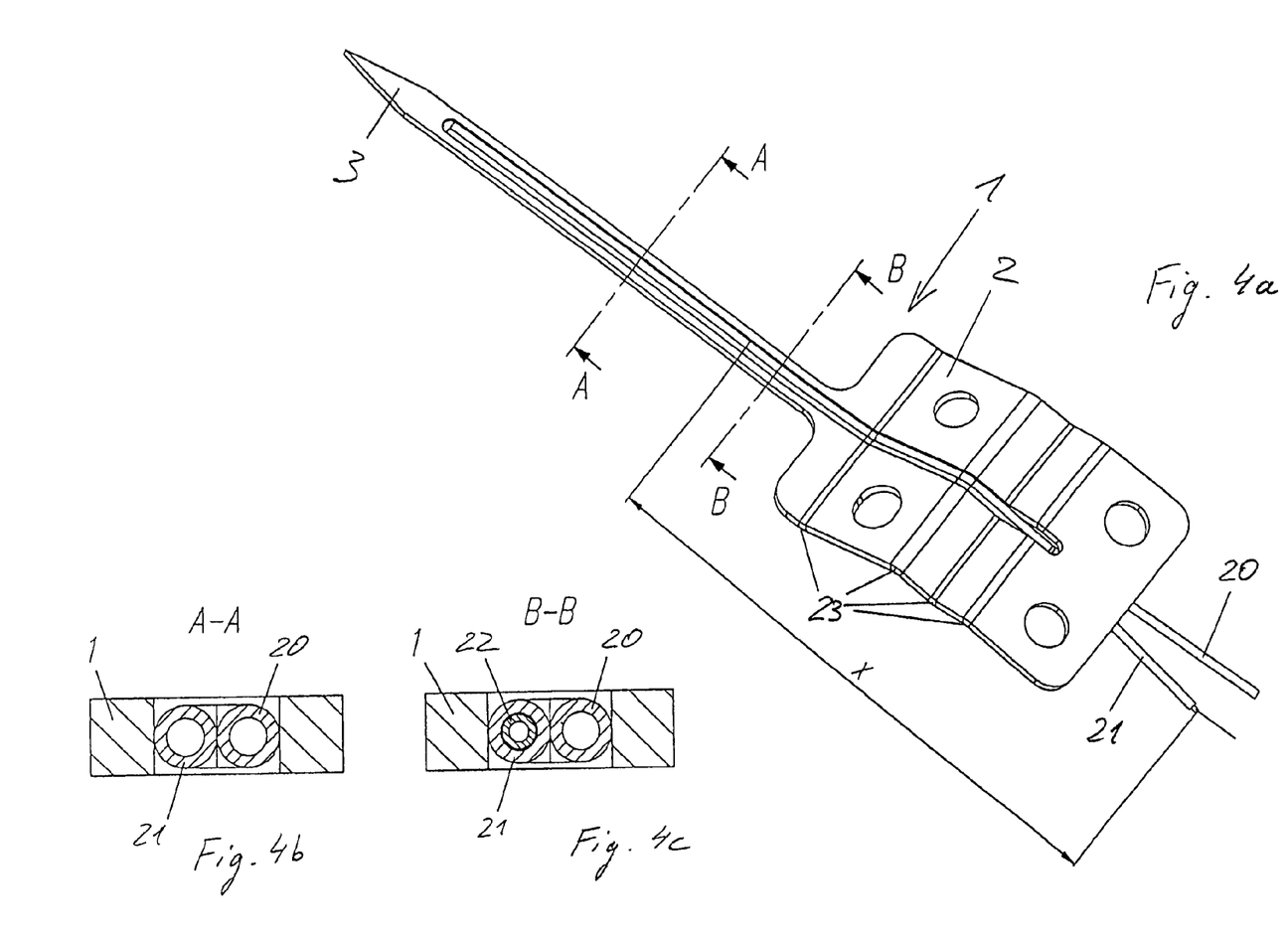
FIGS. 4a to 4c, shows another embodiment of the invention, and FIG. 5, including

FIGS. 4a to 4c show a third illustrative embodiment. Unless stated otherwise below, the third illustrative embodiment corresponds to the second illustrative embodiment.

The hollow lead serving as dialysis membrane is made in one piece and comprises a supply line portion 20 and a discharge line portion 21 which merge into one another at the frame tip 3 by means of the hollow lead 20/21 being bent tight there. The hollow lead 20/21 is a precisely worked hollow thread, preferably a nylon thread, and has the permeability necessary for the dialysis function. Along its entire length, especially in its portion used for dialysis between the widened area 2 of the frame 1 and the frame tip 3, it forms a precisely defined hollow cross section. One of the two portions 20 and 21, in the illustrative embodiment the portion 21, has a greater flow resistance than the otherwise free cross section of flow of the hollow lead 20/21. To achieve the greater flow resistance, a hollow lead 22 narrowing the cross section of flow is integrated in the portion 21 along the length X and imposes the increased flow resistance on the liquid substance. The hollow lead 22, or more generally speaking the flow-increasing insert, which does not necessarily have to be formed as a hollow lead, extends in the portion 21 along the entire length of the widened area 2. Both upstream and downstream, it even extends a short distance past the widened area 2. Toward the frame tip 3, however, it should extend past the area 2 only by a length within which an exchange with the body fluid does not take place.

In the third illustrative embodiment, the hollow lead 20/21 is secured on the frame 1 in a particularly simple way. For this securing, the widened area 2 is kinked several times to and fro transversely with respect to the hollow lead 20/21 so that, as a result, it has a folded configuration. The kink lines are designated by 23. The kinks at the kink lines 23, however, are so flat that the cross section of flow in the hollow lead 20/21 is not affected thereby.

Figure 5A:
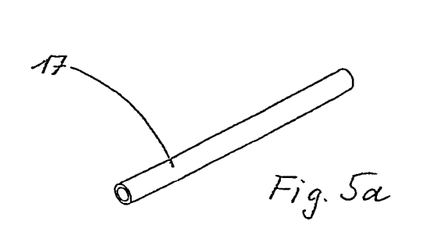
FIGS. 5a to 5e, depicts operational steps in a method according to the present invention.
Figure 5B:
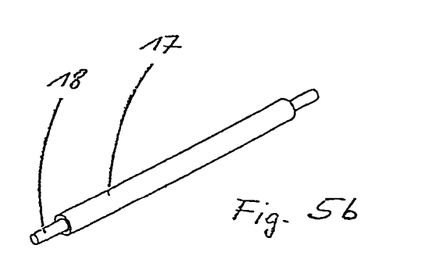
Figure 5C:
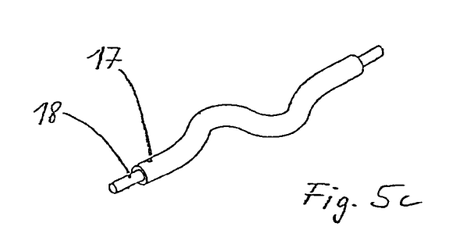
Figure 5D:
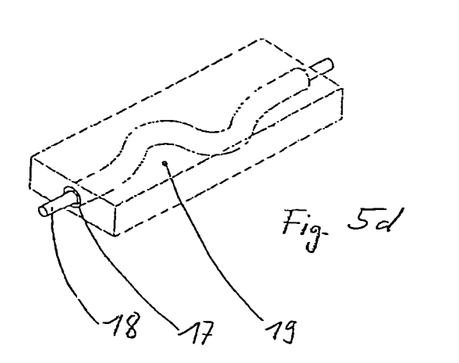
Figure 5E:
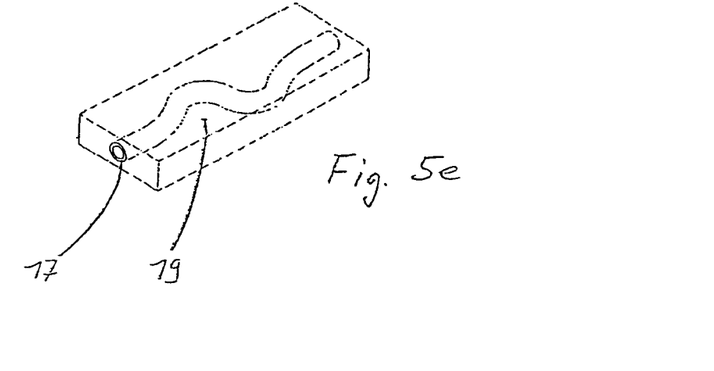

FIGS. 5a to 5e show by way of example the various operations in a method according to the invention for the production of a microdialysis probe. FIG. 5a shows a dialysis membrane in the form of a hollow fiber 17, which can be made of cellulose, for example. Membranes of this kind are flexible and can therefore be bent into various shapes, but conventional membrane materials have a resilience such that the membrane returns to its original shape as soon as the force used to bend the membrane ceases. According to the present invention, as is shown in FIG. 5b, a shaping means is now introduced into the membrane hollow fiber. In the example shown, the shaping means is a filament 18 whose external diameter is slightly smaller than the internal diameter of the membrane hollow fiber. A nylon thread can be used, for example, as the filament. Next, as is shown in FIG. 5c, the membrane hollow fiber is brought into the desired shape by bending the filament 18, for example into a shape defined by the configuration of a probe needle or of a frame for a probe needle. The membrane hollow fiber 17 bears on the filament 18 at least at the bend points. To illustrate the production method, an S-shape has been chosen in FIG. 5c. For practical application of the method according to the invention, for example in the case of a frame of a probe needle as shown in FIG. 2, the membrane hollow fiber is simply bent once through 180° so that two stretches of membrane hollow fiber come to lie next to one another.

In the method according to the invention, the filament is provided merely as an aid for guiding the membrane hollow fiber which is to be routed along a predetermined shape which, for example, is defined by the configuration of a support structure or of a frame. It is also possible, however, that the filament can be bent into various shapes and retains this shape after the force has ceased to apply, as is the case for example in a wire. With a filament of this kind, the membrane hollow fiber can be brought into the desired shape even without a support structure or a frame.

After the hollow fiber membrane has been brought into a desired shape, an adhesive agent is applied at least to a bend point of the membrane hollow fiber. In FIG. 4d, the hollow fiber membrane 17 is shown with the filament 18 and an adhesive agent 19 which has been applied completely around the membrane hollow fiber. For the present invention, however, it is sufficient if the adhesive agent is applied in areas of a bend point in such a way that the membrane can no longer be bent back. At least the rectilinear stretches of membrane hollow fiber do not have to be fixed with the adhesive agent. After application of the adhesive agent 19, the filament 18 is removed from the dialysis membrane. To be able to perform this method step easily, it must be noted that a filament which retains its bent shape, for example a wire, can be easily bent such that it can be withdrawn simply from the shaped membrane hollow fiber, without damaging the membrane and without the adhesive connection coming loose. The shaped part shown in FIG. 5e and comprising the membrane hollow fiber 17 and the adhesive agent 19 can then be finished by means of further processing steps, such as etching, cutting or milling, so that the shaped part too assumes a desired form.

As has been described above, it is also possible in principle to shape a dialysis membrane layer, a dialysis membrane sheet or the like using the method according to the invention. The shaping means used can then be, for example, a metal plate of large surface area, a grid, or several wires or the like distributed across the dialysis membrane layer.

The adhesive agent used can be, for example, cyanoacrylate, silicone or epoxide, but it is also possible to use pressure-sensitive adhesive surface materials, for example in tape form. Moreover, it is possible to use adhesive agents which, for example, can be cured by UV light.

It is also possible, in principle, to employ the method for membranes used in dialysis devices other than a microdialysis probe. Dialysis devices are also of importance, for example, in various chemical or biological test procedures, for example for measuring viscosity or concentration.

The invention has been described by way of illustration on the basis of the embodiments shown. Advantageous configurations and modifications of the concept of the invention, in particular the use of the method according to the invention in devices other than a microdialysis probe, are to be considered as belonging to the scope of the invention.

The invention claimed is:

1. A microdialysis probe comprising a probe body, a supply line and a discharge line for a perfusion solution, a dialysis membrane, and a probe needle for introduction into a tissue, wherein the probe needle comprises a generally elongated frame having multiple partially open recesses formed therein for forming a portion of the supply and discharge lines, and wherein the frame comprises an end remote from the probe body, the end comprising a sharp, pointed tip for introduction into the tissue, and wherein the dialysis membrane comprises a membrane layer that is applied over the multiple recesses forming a portion of the supply and discharge lines.

2. The microdialysis probe according to claim 1, wherein the supply and discharge lines merge into one another at a reverse turn adjacent to the recesses.

3. A microdialysis probe comprising a probe body, a probe needle protruding from the probe body in a distal direction for introduction into a tissue, and a supply line and a discharge line for a perfusion solution, the supply line, the discharge line or both are formed by a dialysis membrane, the probe needle being substantially formed by an elongate frame having a longitudinally extending slit formed therein that extends from a proximate end of the needle to a point proximate a distal end of the needle and divides the frame into two branches; wherein the supply and discharge lines are received between the two branches; wherein the frame comprises an end remote from the probe body, and wherein the end is disposed distally relative to a distal-most portion of the dialysis membrane.

4. The microdialysis probe as claimed in claim 3, wherein the supply and discharge lines merge into one another at a reverse turn crossing the slit.

5. The microdialysis probe as claimed in claim 3, wherein the frame is made in one piece.

6. The microdialysis probe as claimed in claim 3, wherein the frame is at least partly flexible.

7. The microdialysis probe as claimed in claim 3, wherein the frame comprises an end remote from the probe body, the end comprising a sharp, pointed tip for introduction into the tissue.

8. The microdialysis probe as claimed in claim 7, wherein the frame is part of the probe body and wherein the slit is one of inside or adjacent to the probe body.

9. The microdialysis probe as claimed in claim 8, wherein the frame is made of plastic and/or metal.

10. The microdialysis probe as claimed in claim 1, wherein the recesses comprise a first depression forming the supply line, a second depression arranged alongside the first depression and forming the discharge line, the first and second depressions merging at a reverse turn in the area of a tip of the frame, said depressions being formed in a surface of the frame.

11. The microdialysis probe as claimed in claim 10, wherein the first and second depressions are arranged on the same side of the frame.

12. The microdialysis probe as claimed in claim 3, wherein the slit starts in a frame area inside the probe body.

13. The microdialysis probe as claimed in claim 3, wherein the dialysis membrane comprises a hollow fiber arranged in the slit in such a way that it turns at a reverse turn area such that two lengths of hollow fiber lie approximately next to one another.

14. The microdialysis probe as claimed in claim 13, wherein the hollow fiber dialysis membrane is secured on the frame in the reverse turn area.

15. The microdialysis probe as claimed in claim 14, wherein the hollow fiber dialysis membrane is free between the reverse turn area and the probe body.

16. The microdialysis probe as claimed in claim 3, further comprising a separating surface generally between the supply line and the discharge line.

17. The microdialysis probe as claimed in claim 3, wherein the dialysis membrane is partially surrounded by a non-permeable layer along a length forming the supply or discharge line.

18. The microdialysis probe as claimed in claim 3, wherein several flat projections protrude over the slit along the surface of the frame.

19. The microdialysis probe as claimed in claim 13, wherein the hollow fiber protrudes from the probe body.

20. The microdialysis probe as claimed in claim 3, wherein the dialysis membrane extends along the length of the slit.

21. A microdialysis probe comprising:
a probe body;
a probe needle protruding from the probe body in a distal direction for introduction into a tissue; and
a supply line and a discharge line for a perfusion solution, wherein the supply line, the discharge lines or both are formed by a dialysis membrane;
wherein the probe needle is substantially formed by a generally flat elongate frame;
wherein the frame comprises a longitudinally extending slit that extends through the frame from a proximate end of the needle to a point proximate a distal end of the needle;
wherein the frame comprises an end remote from the probe body; and
wherein the dialysis membrane is located in the slit and extends along the frame such that a distal-most portion of the dialysis membrane is substantially at or short of the end of the frame.

22. The microdialysis probe of claim 21, wherein the frame has a rectangular cross-section.

23. The microdialysis probe of claim 1, wherein the recesses are formed on a side face of the frame that extends in the longitudinal direction of the frame.

24. The microdialysis probe of claim 23, wherein the recesses extend in the longitudinal direction of the frame.

25. The microdialysis probe of claim 24, wherein the dialysis membrane is formed as a sheet, and wherein the sheet lies substantially flat on the side face of the frame having the recesses formed therein.

26. The microdialysis probe of claim 24, wherein the dialysis membrane is formed as a hollow fiber.

27. The microdialysis probe of claim 21, wherein the dialysis membrane is a hollow fiber, and the slit has a width that is greater than or equal to twice an external diameter of the hollow fiber.

28. The microdialysis probe of claim 21, wherein the dialysis membrane is a hollow fiber, and the slit has a height that is greater than or equal to an external diameter of the hollow fiber.

29. The microdialysis probe of claim 21, wherein the slit is at least partially formed by side walls having a concave shape.

30. The microdialysis probe of claim 1, wherein the tip is formed by a tapering of opposite faces of the frame in a direction of a center of the frame.

31. The microdialysis probe of claim 1, wherein the membrane layer is connected to the frame across an entire surface edge and all around the recesses.

* * * * *